United States Patent [19]
Feder et al.

[11] Patent Number: 5,521,812
[45] Date of Patent: May 28, 1996

[54] EMERGENCY INFORMATION APPARATUS AND METHOD

[75] Inventors: David L. Feder, 1222 W. 62nd St., Kansas City, Kans. 64113; Milton L. Goff, Ramona, Calif.

[73] Assignee: David L. Feder, Kansas City, Kans.

[21] Appl. No.: 239,242

[22] Filed: May 6, 1994

[51] Int. Cl.⁶ .................................................. G06F 159/00
[52] U.S. Cl. ......................................................... 364/400
[58] Field of Search ........................ 364/413.01, 413.02, 364/413.03, 400

[56] References Cited

U.S. PATENT DOCUMENTS

| | | |
|---|---|---|
| 3,845,250 | 10/1974 | O'Brien . |
| 4,303,395 | 12/1981 | Bower . |
| 4,583,524 | 4/1986 | Hutchins . |
| 4,588,383 | 5/1986 | Parker et al. . |
| 5,025,374 | 6/1991 | Rolzen et al. ...................... 364/413.01 |
| 5,059,126 | 10/1991 | Kimball .................................. 434/308 |
| 5,086,391 | 2/1992 | Chambers . |
| 5,088,037 | 2/1992 | Battaglia . |
| 5,185,857 | 2/1993 | Rozmanith et al. ..................... 395/148 |
| 5,274,560 | 12/1993 | Larue ...................................... 364/444 |

*Primary Examiner*—Donald E. McElheny, Jr.
*Attorney, Agent, or Firm*—Steven C. Sereboff

[57] ABSTRACT

Devices and methods for providing emergency information. This emergency information device is a portable unit which may be carried to an emergency site. It is operative in response to parameter entries by the rescuer according to the victim's condition to provide sequential procedural displays of medical standard rescue steps for assisting the rescuer in carrying out the correct rescue operation. The standard rescue procedure is stored in a microprocessor which, if necessary, can be re-programmed to update to a new rescue standard procedure. It includes a recall feature operative for reverse searching of any desired step in the display if the condition of the victim changes during the rescue operation. Additionally, distinct tone signals are emitted at selected steps of the rescue operation procedure to assist the rescuer in memorizing and conducting such steps in the rescue.

14 Claims, 5 Drawing Sheets

EMERGENCY INFORMATION APPARATUS AND METHOD

BACKGROUND OF THE INVENTION

1. Field of the Invention

The present invention relates generally to portable devices which provide useful information in medical and other emergency situations.

2. Description of Related Art

In any emergency operation, such as in the rescue of an unconscious victim, it is of paramount importance for the individuals involved to take the proper actions as soon as possible. Normally, if proper rescue operations are applied to a victim, the chances of survival or recovery of the victim are much improved. In order to carry out many rescue operations effectively, the rescuer must follow the steps set forth in any of the standard medical rescue manuals. The proper procedure is generally based upon the particular condition of the victim.

Standard rescue procedures are well developed in the medical field and are beyond the scope of this disclosure, except so far as may be necessary to explain the nature and application of the present application. Studies have shown that even amongst professional rescue operators such as paramedics, firemen, and nurses, relatively few people can remember the proper rescue sequence or procedure precisely. This is further complicated because the "standard" procedures frequently change as they are refined and new methodologies are introduced.

Even more importantly, a paramedic, fireman, nurse or other emergency medical technician is generally not available in the critical initial moments of an emergency. Rather lay rescuers, i.e. ordinary individuals, generally discover emergencies, and these people are responsible for both initiating the proper procedures and determining whether additional assistance from professionals is necessary.

In general, the standard procedures have become more complex, and more procedures have been created for a growing number of emergencies. As procedures become more and more complex, potential rescuers have more and more difficulty in obtaining familiarity with them and memorizing them.

Moreover, the ability of a rescuer to recall and employ the proper emergency procedure is further hampered by the chaotic circumstances typically surrounding an emergency situation.

The prior art has seen varied approaches to the handling of emergency instructions or to the use of audible instructions. The prior art systems have included use of instruction booklets having indices in which the particular emergency has to be located; then pages flipped locate the emergency; and read step by step while trying to perform the emergency with one hand and constantly going back to reread the instructions. The prior art also has included sophisticated computer instructions that are activated by a particular code on a telephone to give a caller instructions as to how to fill out a bank deposit, how to call a particular bit of information regarding insurance policies or the like.

Attempts have been made to provide devices to assist in providing emergency information to ensure that a rescuer performs the rescue operation properly. However, most of these have been devices dedicated to just one type of emergency—cardio pulmonary resuscitation (CPR). One of such devices is shown in U.S. Pat. No. 4,451,158 to Selwyn et al. Selwyn's device is in the form of a timer with various coded pattern displays at predetermined time intervals to indicate various stages in the rescue operation. The main drawback of the device is that confusion may still arise for the rescuer to memorize which procedural step is related to which code.

Another device, such as that shown in U.S. Pat. No. 4,588,383 to Parker et al., provides voice instructions solely for the rescuer to carry out the CPR rescue operation. Other portable CPR-prompting devices have been disclosed in U.S. Pat. No. 4,588,383 to Parker et al., U.S. Pat. No. 4,583,524 to Hutchins, and U.S. Pat. No. 5,088,037 to Battaglia.

An emergency audible instruction apparatus for a fire extinguisher is disclosed in U.S. Pat. No. 4,303,395 to Bower. Such a device provides audible instructions which instruct a user in handling a fire emergency. The device is activated automatically when the fire extinguisher is removed from its base. Bower suggests that a device embodiment storing multiple instructions may be included with a dial selector for selecting a particular emergency. However, unlike the CPR-prompting devices, however, the Bower device is not portable, and suggests purely mechanical means for providing a portable solution.

A generalized manual key operated message generator is described in U.S. Pat. No. 3,845,250 to O'Brien. However, this device is not portable nor adapted for emergency use. To retrieve a message, the user presses a series of keys to assemble a complete message upon prerecorded parts.

U.S. Pat. No. 5,086,391 describes a medical alert system for domestic use comprising two major components, a device worn about the neck and a home computer. The device worn about the neck and the home computer reciprocally communicate with one another to provide the wearer of the device, as well as an attendant of the device, both instructions for care and a method to call for emergency help. The home computer contains an audio synthesizer and a voice amplification device to communicate verbally to the individual. The device may be used to summons an ambulance from a remote location if the injured person is unable to reach a telephone.

As can be seen, most of the known devices are bulky in size, not portable to be located conveniently beside the victim at the rescue site, provide very limited information and are complex to operate. The principal object of the present invention is to provide a portable device which can be conveniently located beside a victim or near an emergency site to assist the rescuer to carry out the rescue operation. It is another object of the present invention to provide an emergency information device which provides step by step instructions sequentially in response to the condition of the victim. It is another object of the present invention to provide a rescue administration aid device operative to assist one or two rescuers to perform the required rescue operation on a victim of a selected age group. It is yet another object of the present invention to provide a rescue administration aid device which is operative to recall any selected step in the rescue operation by the rescuer. It is still a further object of the present invention to provide a rescue administration aid device in which the rescue instructions can be easily and inexpensively modified, if necessary, to update to a new rescue operation standard.

These objects and others are provided in the emergency information apparatus of the present invention.

SUMMARY OF THE INVENTION

The invention is directed to apparatuses and methods for providing emergency information. According to the invention, there is provided a battery powered apparatus into which an untrained user may insert a prerecorded program medium. The apparatus automatically begins playback upon selection of any one of a plurality of programs identified on the apparatus. The apparatus includes playback selectors to control playback of the programs. The program medium includes programs in two languages, and can switch substantially instantaneously between languages. The apparatus automatically powers off at the end of playback.

Programs may also include data which is utilized by the apparatus to link programs and otherwise control playback.

DESCRIPTION OF THE DRAWINGS

These and other advantages of the present invention are best understood with reference to the drawings, in which.

DETAILED DESCRIPTION OF THE PREFERRED EMBODIMENT

Figure 1:
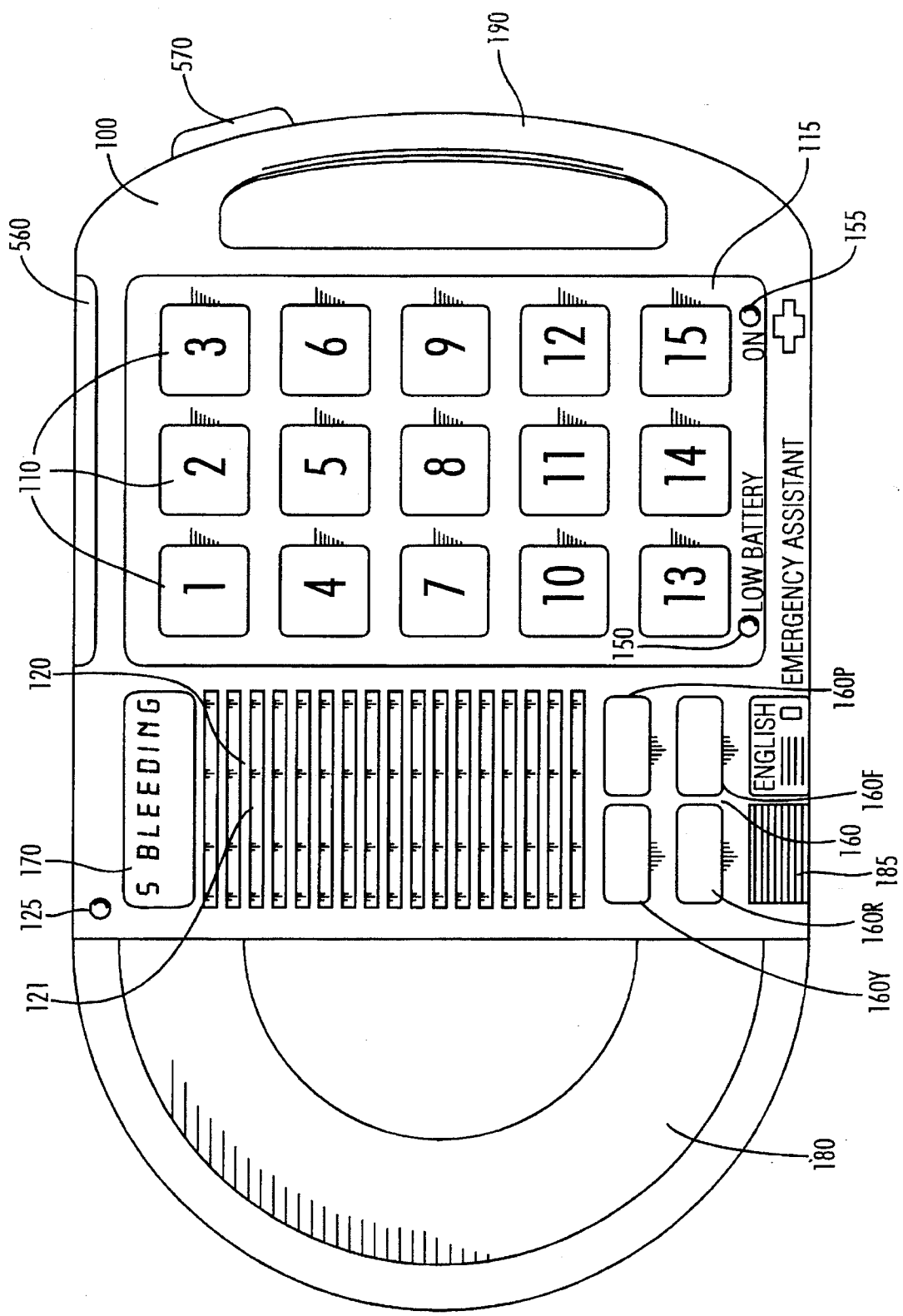
FIG. 1 is a partial elevation of an emergency information apparatus in accordance with the present invention.

An emergency information apparatus according to an embodiment of the invention is described. Throughout this description, the preferred embodiment and examples shown should be considered as exemplars, rather than limitations on the method and apparatus of the present invention.
External Aspects Referring now to FIG. 1 there is shown a partial elevation of an emergency information apparatus in accordance with the present invention. The external portion of the apparatus is comprised primarily of a casing 100. The casing 100 is preferably of a rigid material, such as hard plastic, PVC, or the like. In addition, the casing and the items disposed in and within the casing 100 are, together, water resistant, such that water will not seep into the internal portion of the apparatus and induce electrical shorts or corrosion. This is beneficial so that the apparatus may be used, for example, in the rain, or during fire emergencies when water is being used to dowse the fire. The bottom of the casing 100 (not shown) preferably includes shock absorbing pads, such as rubber pads embedded within the casing 100 and exposed at the outer edge of the casing 100 to reduce shock and vibration when the apparatus is set down.

On the left side of the apparatus there is a hinged compartment 180. The compartment 180 is in a closed and locked position, as shown. The compartment 180 may be opened through a release (not shown), which may be on the side or top of the apparatus as known in the art. The compartment 180 is adapted for receiving a program medium, preferably a compact disc (CD) (not shown). When open, the compartment 180 may received a CD, and when closed, the compartment 180 holds the CD within the apparatus.

While a CD is preferred as the program medium, other media are generally suitable. These media preferably are of a standard form and storage format, such as micro cassette, floppy disk, DAT, flash memory or ROMs on a PCMCIA card. However, it is believed that the CD format has at least six advantages over these others. First, CDs are relatively inexpensive to produce and manufacture. Second, CDs are resistant to corrosion and environmental influences. Third, the typical user is comfortable with the use of CDs, for example their insertion into a player and operation of a CD player. Fourth, playback of a CD may be quickly moved from one area to another, permitting rapid movement between programs and instructions. Fifth, a standard audio CD stores information in stereo, thereby permitting rapid switching between languages on a bilingual CD, as explained below. Sixth, updated CDs can be exchanged for old CDs having outdated information.

The CD is preferably within accepted standards as to form. The CD may be manufactured using well known methods. The CD stores emergency information in a plurality of programs, and each program is made up of one or more instructions. A program may include the audio portion of the emergency information to be presented to a user. This aspect is like that of typical CDs. However, unlike typical CDs, and as explained below, the programs may also include dual tone multifrequency (DTMF) data. This DTMF data provides control signals to the emergency information apparatus, and may be used, for example, so that a particular program, upon its end, causes an indicated next program to be played.

In the disclosed embodiment, there are provided five rows of three program selectors 110. The program selectors 110 are used for selecting and thereby starting the playback of programs stored on a CD which has been properly inserted into the compartment 180. The number of program selectors 110 is not critical, although several should be provided so that several emergencies may be addressed by any one CD. To further control playback, and as explained further below, there are also provided several playback selectors 160, including a pause key 160H, a reverse key 160R, a forward key 160F and a continue play key 160P. The program selectors 110 and the playback selectors 160 are preferably push buttons.

Preferably, there is disposed in the casing 100 a light sensor (not shown). The light sensor is of the typical variety. The program selectors 110 and playback selectors 160 preferably are backlit, and the lights for the selectors 110, 160 are preferably coupled to the light sensor, such that the selectors 110, 160 are automatically illuminated when the ambient light falls below a selected threshold. The design and construction of such circuits are well within the ability of those of ordinary skill in the art, so further description is not provided.

A nearly limitless number of programs may be used with the apparatus. Simply by changing CDs, a new set of programs may be made available. To accommodate this flexibility, the program selectors 110 are preferably labelled with numbers 1–15, and these numbers correspond to programs on a CD (which is adapted for use with the apparatus). Programs may include instructions relating to AIDS/HIV, bloody nose, bumps and bruises, burns, choking, CPR, dental injuries, drowning, earthquakes, electric shock, external bleeding, eye injuries, fires, fractures and dislocations, frostbite and hypothermia, heart attack, heat emergencies, inset stings and bites, internal injuries, muscle cramps, poisoning; rescue breathing, seizures and shock, stroke, spinal injuries, sprains and strains, and emergency action principles.

With each CD, there is preferably provided a removable overlay 115. The overlay 115 is adapted to be placed over and around the program selectors 110. The overlay 115 labels the program selectors 110 in accordance with the programs stored on the CD. Thus, by scanning the overlay 115, the user can determine which program selector 110 to press to begin playback of a desired program. The overlay 115 is preferably a thin piece of plastic, with the labels being resistant to erasure from typical use of the apparatus.

Alternatively, the program selectors 110 are stenciled with the appropriate program name. Aftermarket CDs may be provided with appropriately labelled for covering over the stencils.

The apparatus further includes a speaker 120 for playing back the audio portion of the programs stored on the CD. The speaker 120 is preferably disposed behind a grill 121. The grill 121 prevents damage to the speaker 120 from rigid objects which could puncture and thereby damage the speaker, and preferably prevent water from reaching the speaker 120. Disposed in the casing 100 and preferably near the speaker 120 is a volume control 125. The volume control 125 may be operated by the user to adjust the volume of the program playback from the speaker 120. Preferably, either by a mechanical stop or electrical cut-off, the speaker's volume may not be reduced below a predetermined threshold. This prevents the volume control 125 from being set so low that the user is not aware that a program is playing.

The speaker 120 is shown in FIG. 1 as disposed substantially above the compartment 180. However, if the speaker is deep, then it would be preferable to swap the positions of the speaker 120 and the playback selectors 160 with the positions of the program selectors 110.

Once a program selector 110 has been pressed and the selected program has begun to play, the number of the program as associated with the program selector 110 and the name of the program is displayed on a display 170. In FIG. 1, it is shown that program number 5 relating to "bleeding" has begun playback. The display 170, is preferably a backlit liquid crystal display, although any device which is compact and can display the program number is suitable. This may include a series of LEDs or even a mechanical means.

To aid in portability, the apparatus is further provided with a handle 190. The handle 190 is adapted for easy holding by the user. Because most people are right handed, the handle is disposed on the right side of the apparatus. Furthermore, the weight of the apparatus is preferably balanced to ease any potential strain on the holder of the handle 190.

Also disposed within the casing 100 are two indicator lamps 155, 156. One indicator lamp 155 is provided to indicate when the apparatus is powered-on. The other lamp 156 is provided to indicate when the battery is low. These lamps are preferably red and amber LEDs, respectively, although other colors and other types of indicators may be suitable.

As explained further below, the CD may include programs having a multilingual audio portion. Preferably there is a language selector 185 in the casing. The language selector 185 is preferably a two-position (A and B) switch having labels which turn with the switch. More preferably, the language selector 185 allows selection of any of four languages. This labelling is preferably on the overlay 115. To select a language to be played, the language selector 185 is set to one of its two positions. Thus, emergency information may be provided by the apparatus in a multiplicity of languages, simply by moving the language selector 185, or changing CDs (and the accompanying overlay 115).

Figure 5:
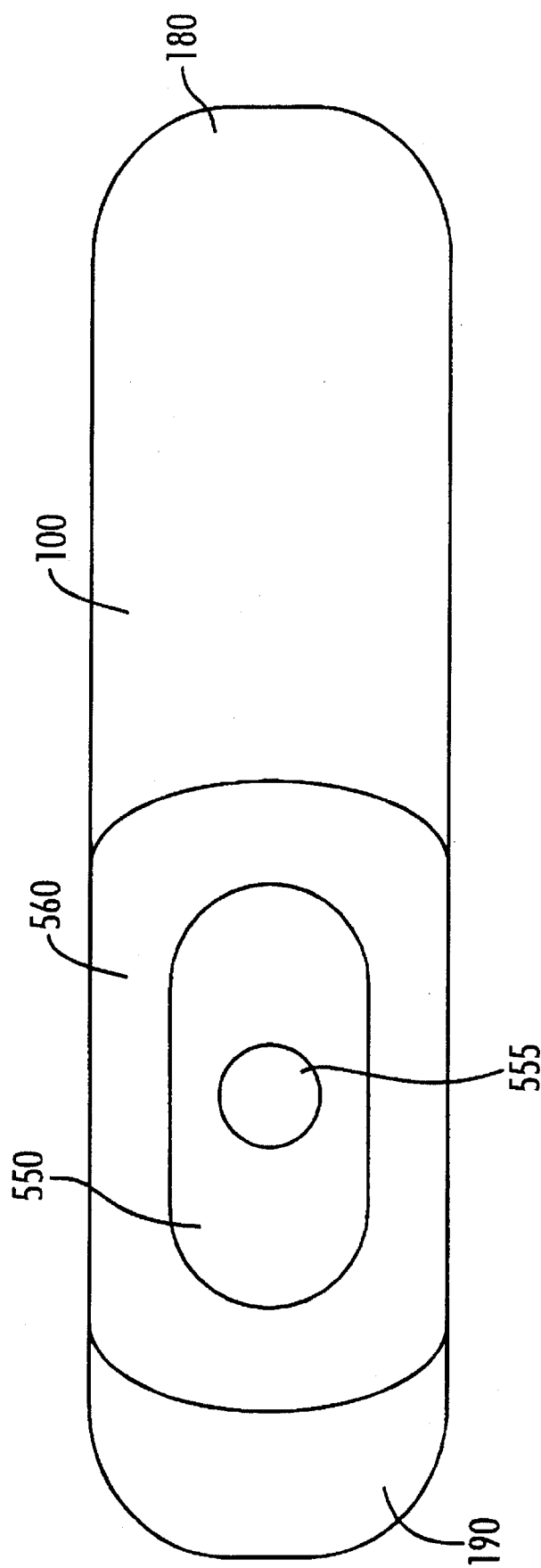
FIG. 5 is a back side view of the apparatus of FIG. 1.

A flashlight is also preferably included within the apparatus. Referring now to FIG. 5, there is shown a side view of the apparatus. In this view, the handle 190 is on the left and the compartment 180 is on the right. Centrally located on the side of the casing 100 and towards the left on FIG. 5 is a flashlight 550. The flashlight 550 includes a bulb 555 which is aimed away from the casing 100 at about a 90° angle from the longitudinal axis of the handle 190. Preferably, the flashlight 550 has an independent power supply, with a power switch 570 disposed in the casing 100 on the handle 190. The flashlight 550 is preferably arranged such that when the batteries wear out, the front facing of the flashlight 560 is removed and the batteries (not shown) are replaced.

In another embodiment, the flashlight 550 comprises an ordinary disposable flashlight which slides into the casing 100. Accordingly, when the flashlight's batteries wear out, the flashlight 550 is replaced.

Alternatively, the flashlight 550 is further integrated with the apparatus. In this embodiment, the flashlight draws power from the power subsystem 204. This ensures that the flashlight has sufficient power. The flashlight could also be coupled to the light sensor, such that the light level is adjusted automatically.

The flashlight 550 is preferably located as shown to permit the user to manipulate the selectors 110, 160 while aiming the flashlight away from himself. Since the apparatus may be used while the user is walking, the provision of the flashlight is seen to be quite beneficial in low light environments.

Internal Aspects

Figures 2A, 2B:
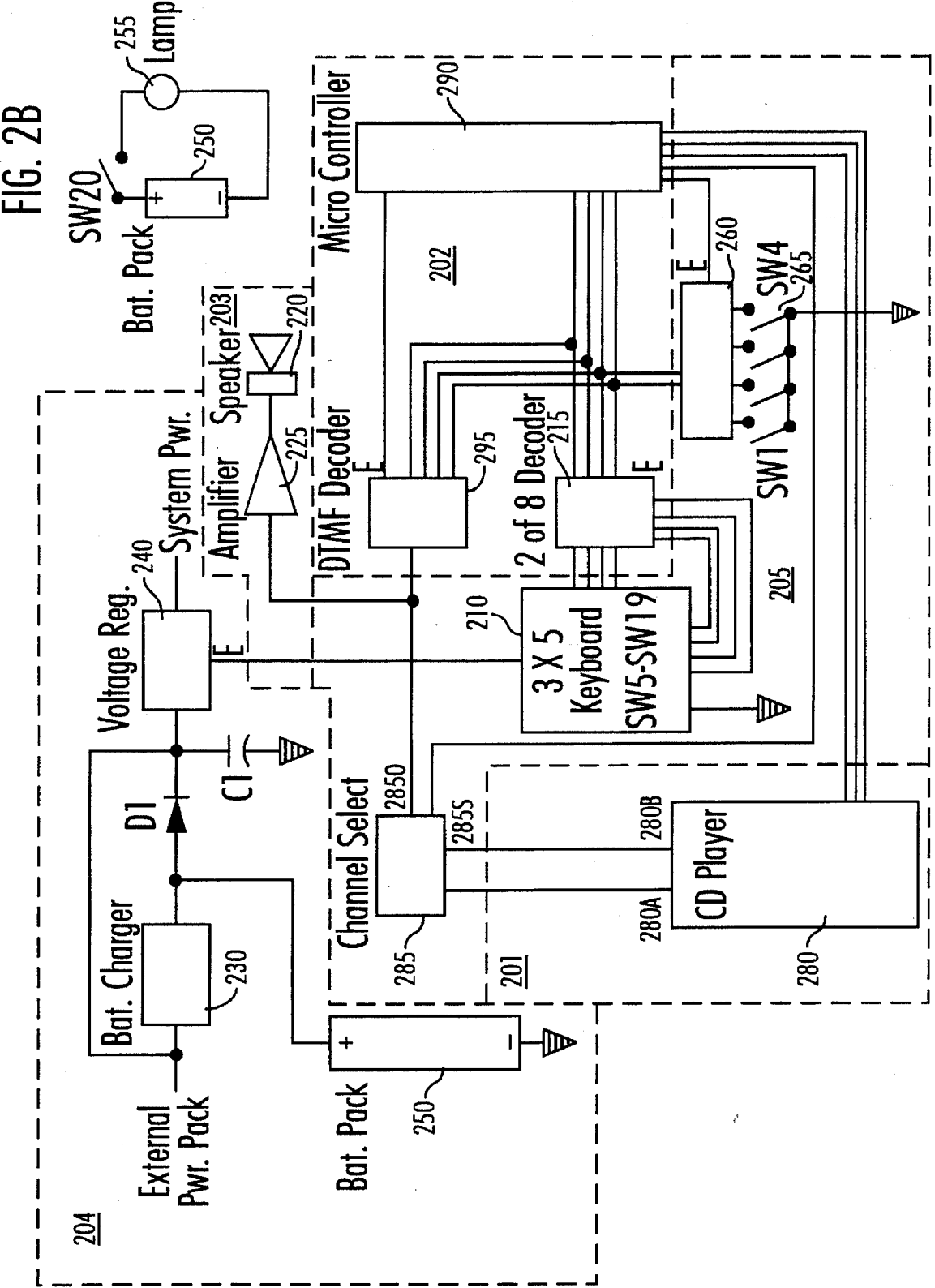
FIGS. 2A and 2B are electronic block diagrams of the apparatus of FIG. 1.

Referring now to FIGS. 2A and 2B, there are shown electronic block diagrams of the apparatus of FIG. 1. The electronics of the apparatus may be separated into five logical subsystems: a playback subsystem 201, a control subsystem 202, an input subsystem 205, an output subsystem 203 and a power subsystem 204.

The playback subsystem 201 preferably comprises a CD player 280. The playback subsystem 201 is at least partially disposed within the compartment 180. In the preferred embodiment, the compartment 180 opens into the CD player 280, and forms the cover for the CD player 280. The CD player 280 may be a standard compact, portable CD playback device, such as the Philips CD 4000.

The input subsystem comprises a 3×5 keyboard 210, a 4×1 switch bank 265, a latch 260, and a channel selector 285. The program selectors 110 are coupled to the 3×5 keyboard 210. The playback selectors 160 are coupled to the switch bank 265, and the switch bank 265 is coupled to the latch 260. When a playback selector 160 is pressed while the power is on, the identity of the pressed selector 160 is latched by the latch 260.

The CD player 280 provides output on channel lines 280A and 280B. In a typical CD player, the channel lines 280A, 280B would carry respectively the left and right channel of a stereo recording. However, in the preferred embodiment of the present invention, separate programs (e.g., the same program in two languages) are stored in each of the two channels on the CD, and the channel lines 280A, 280B carry the respective programs. The channel selector 285 receives the outputs from the CD player and under the control of the language selector 185, selects one of the two signals 280A, 280B and outputs that signal on the channel select output 2850.

The control subsystem 202 comprises a microcontroller 290, a 2 of 8 decoder 215, and a DTMF decoder 295. The microcontroller 290 is preferably an Intel 8084 8-bit 3-port microprocessor having on-chip memory (ROM and RAM), and at least one I/O port. One port of the microcontroller 290 is coupled to the CD player 280. The data bus of the microcontroller 290 is coupled to the two of eight decoder 215, the latch 260, and the DTMF decoder 295.

The microcontroller 290 preferably includes a program for operating the apparatus in ROM. Although a particular microcontroller is disclosed, no microcontroller is considered better than any other for use in the apparatus. Because programs will be different for different microcontrollers, a complete program is not disclosed. However, one of ordinary skill in the art having knowledge of microcontroller programming could use this disclosure, including the description of the operation of the apparatus below and the drawings, to produce an appropriate program in a short period of time.

The 2 of 8 decoder 215 decodes the output of the keyboard 210. The microcontroller 290 determines which key on the keyboard 210 is being pressed using conventional techniques, such as periodic scanning. The microcontroller 290 detects the activation of a playback selector 160 by scanning the latch 260. The microcontroller 290 also scans the DTMF decoder 295. Each of the latch 260, the 2 of 8 decoder 215 and the DTMF decoder 295 are enabled by the microcontroller 290 by an enable line, labeled as "E" for each of these devices on FIG. 2A.

The DTMF decoder 295 may be of conventional design, such as a Motorola MC145436P. The DTMF decoder 295 converts tones received from the channel selector 285 to digital (i.e., binary) data, which the microcontroller 290 can process.

The DTMF data stored on a CD is preferably encoded. A particular coding scheme is not preferred. However, the coding scheme preferably provides a set data format. For example, the first several bits might represent a command, such as "jump to another track on the CD," and the next several bits might represent data for the command, such as an address for the jump. Such a coding scheme could be employed to provide any number and type of control commands. Preferably, a number of commands are provided. One preferred command causes playback to move to another location on the disk. Such location is preferably included in the DTMF data. Another causes playback to end. Yet another alters playback volume. Another powerful command pauses playback until an input is received. This last, "conditional" command would be useful for providing CPR instructions, since a rescuer administering CPR should be doing steps at particular times, and different steps should be taken depending on the condition of the victim. Thus, one program selector 110 could be generally labelled "CPR" and when pressed, the program would ask a question, such as "Is the victim a child? If yes, press the 'yes' key." By providing a program selector labelled "Yes," the apparatus can be used to determine whether the victim is a child, and then play the appropriate program.

DTMF data may be stored at the beginning of the CD to represent index information of the programs and instructions on the CD. Also, if the apparatus is provided with an appropriate display as shown in FIG. 1, the DTMF data could include text for display during program playback.

The microcontroller 290 is coupled to the CD player 280 for program and instruction selection as well as control of stopping and pausing of programs.

To include more than two languages, the CD may include the programs for plural languages in the same channel. These programs are preferably placed on the CD, either at predefined positions, or else at positions included in the index information. For example, for a CD capable of holding up to 72 minutes of audio programs, the CD can store four programs of 36 minutes each. Manipulation of the language selector results in either the control subsystem moving to another track or the channel selector 285 switching channels, or both.

The output subsystem comprises an amplifier 225 coupled to a speaker 220. The amplifier receives the output from the channel selector 285. The amplifier may be, for example, a five watt audio amplifier, and the speaker 220 may be a conventional, low weight speaker. As mentioned above, the volume control 125 is used to adjust the volume of the speaker. Although not shown, those of ordinary skill will recognize that the volume control 125 may be coupled to the amplifier in the conventional manner.

Alternatively, the volume control 125 may be coupled to the microcontroller 290, for example via an I/O port of the microcontroller 290. The microcontroller would also be coupled to the amplifier 225. The microcontroller would be programmed to scan the setting of the volume control 125, and, based upon the setting of the volume control 125, would control the amplifier's output.

Power for the apparatus is provided by the power subsystem 204. The power subsystem comprises a battery pack 250, a battery charger 230, a diode D1, a capacitor C1, a voltage regulator 240 and a lamp 255. The battery pack 250 is preferably a NiCAD type cell.

The battery charger 230 may be of the conventional type with a connector for external power in the form of an ordinary household two-prong jack (not shown). Preferably, this jack can be flipped out from the surface of the casing 100 at the back of the apparatus and plugged directly into an ordinary electrical outlet. The batter charger 230 is coupled to the battery pack 250. Thus, when the apparatus is plugged into an outlet, the batter charger 230 charges the battery pack 250 and supports the apparatus.

Also coupled to the battery pack 250 via a switch SW20 is a lamp 255. This lamp 255, is coupled to the indicator 155 in the casing to indicate when the apparatus is fully active.

The voltage regulator 240 provides power conditioning to prevent the sensitive circuitry of the various electronic components from being damaged. As shown in 25 FIG. 2A, the voltage regulator 240 is coupled to the battery pack 250, the battery charger 230, the external power supply, and to the 2 of 8 decoder 215. The keyboard 210 always receives power from the voltage regulator. Thus, even when the apparatus is in a power-off state, pressing a program selector 110 activates a switch in the keyboard 210 which is decoded by the 2 of 8 decoder 215.

The 2 of 8 decoder 210 preferably includes electronic switches (not shown), which control power to the other components of the apparatus. The electronic switches are open when the apparatus is in a power-off state. However, the electronic switches are controlled by the 2 of 8 decoder 215 in a way that when the decoder 215 detects a signal from the keyboard 210, the electronic switches close. Thus, when a program selector 110 is pressed, the apparatus enters a power-on state without the user having to utilize a separate power switch.

Operations of Apparatus

Figure 3:
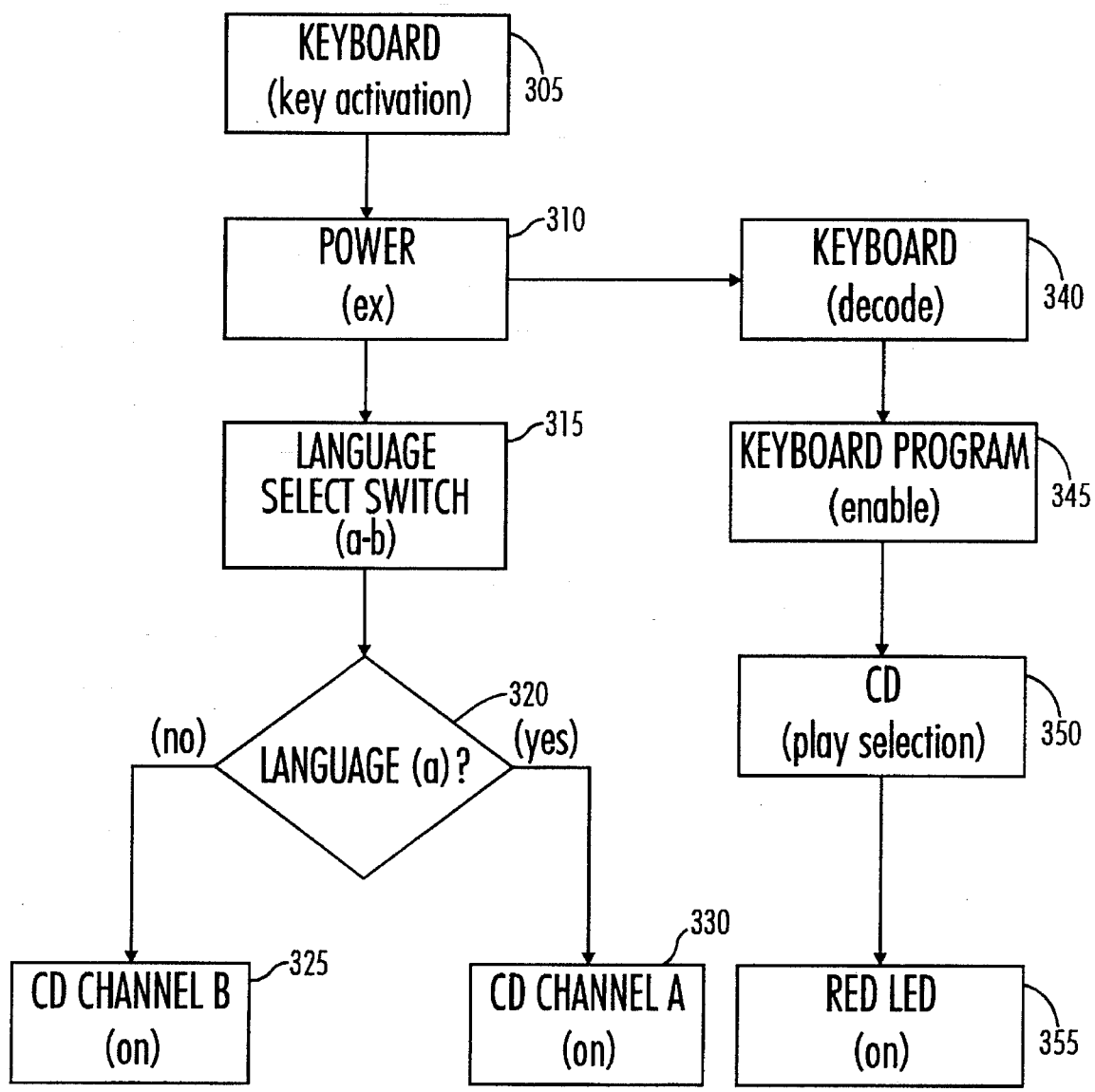
FIGS. 3 and 4 are flow chart(s) of the operations of the apparatus of FIG. 1.

Referring now to FIG. 3 there is shown a flowchart for the operation of the apparatus from the power-off state.

From the power-off state, the process begins at step 305 with activation of the keyboard 210 upon the depression of one of the program selectors 110. The 2 of 8 decoder 215 detects the pressing of a program selector 110 as described above, and allows power to flow to the other components of the apparatus. Next, two separate processes begin and run simultaneously.

In one process, the apparatus determines which language has been selected (Step 315). If the language selector 185 is in the A position, then the program in the CD's channel A will be provided as the output of the channel selector 285. Alternatively, if the language selector 185 is in the B position, then the output of the channel selector 285 will be from the B channel of the CD (Step 325).

It can be seen that provision of the language selector 185 permits very rapid changing between two languages. This is because the program in the first language is played at the same time as the program in the second language, and switching between the programs is substantially instantaneous upon the change of the position of language selector 185.

Also subsequent to power-on (Step 310) the keyboard 210 is decoded (Step 340) by the 2 of 8 decoder 215. The microprocessor then accepts the decoded keyboard information representing the identity of the selected program selector 110 (Step 340). Next, in Step 345, the microcontroller uses the identification of the selected program selector 110 to enable playback of the selected program from the CD player.

This may be achieved in at least two ways. Preferably, the CD contains DTMF encoded index information located at a predetermined position which is played back upon power-up. Upon power up, the microcontroller causes the CD player to begin playback of the DTMF encoded index information. The index information is received by the microcontroller 290 via the DTMF decoder 295. The microcontroller 290 identifies the desired program to play and commands the CD player 280 to play the program based upon the index information.

Alternatively, the programs of every CD may be placed at fixed positions on the CDs. In this way, for all CDs, the programs are stored at consistent relative positions. For example, program 3 on every CD would be in the same place.

After playback has been enabled, the CD player 280 will then play the prerecorded program on the CD (Step 350). Also, the power-on lamp 255 is activated (Step 355).

Preferably, the DTMF encoded index information also includes the positions of each instruction within each program. Once the CD begins playback, the various playback selectors 160 may be manipulated to pause the play, reverse by one instruction, advance by one instruction, or resume play. Preferably, each instruction is made as short as possible, to permit easy movement by the user through the program using the reverse selector 160R and forward selector 160F. If the location of the instructions is not known, as would be the case in simpler embodiments, then the reverse selector 160R and forward selector 160F would move playback by a set amount, such as one track.

Figure 4:
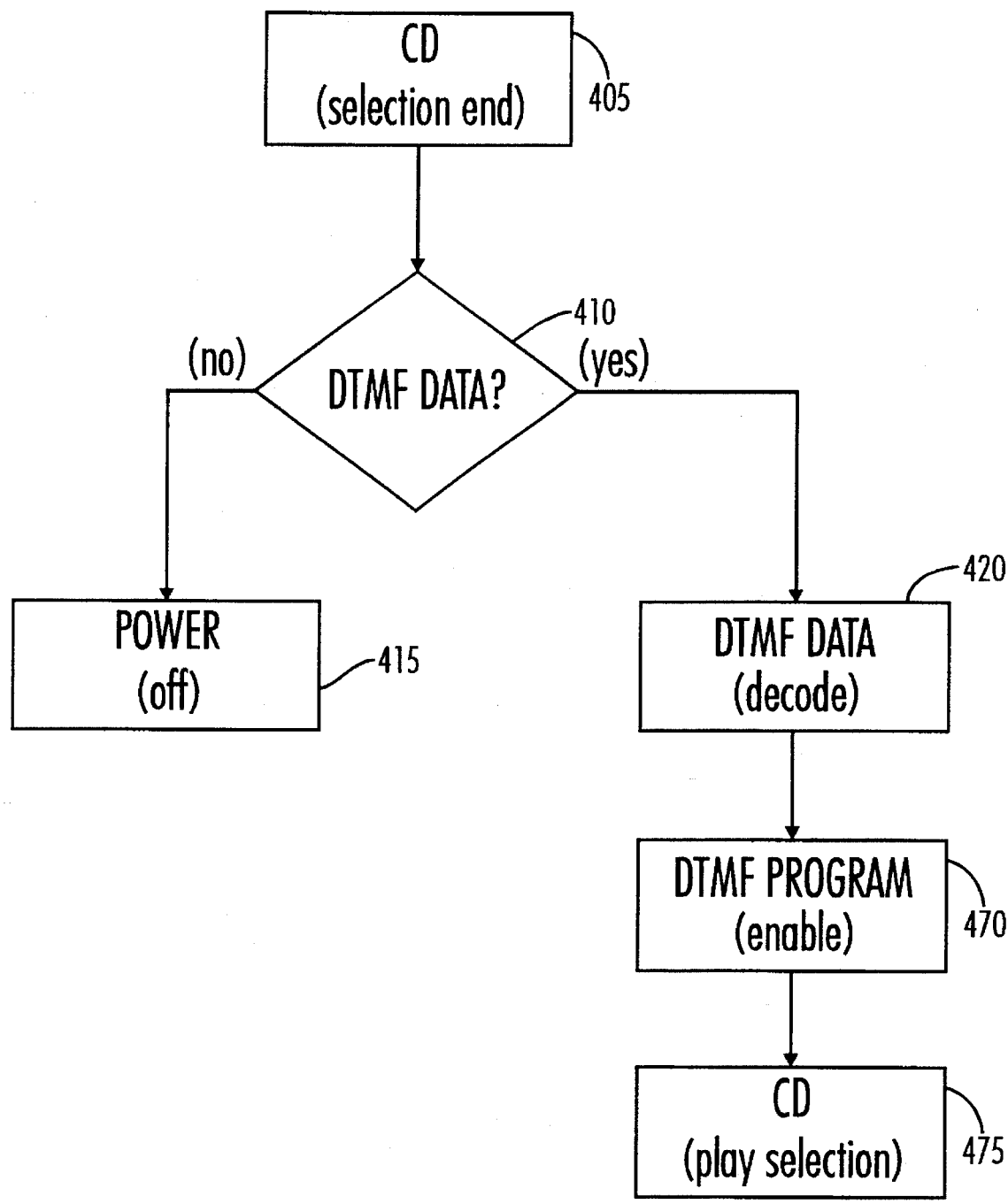

Referring now to FIG. 4, there is shown a flow chart for the operation of the apparatus at the end of a program. When playback of a program on the CD ends (Step 405), normally the apparatus will return to its power-off state (Step 415) and the power indicator 255 is turned off. However, if DTMF data is in the program at the end of the program (Step 410) then the DTMF data is decoded by the DTMF decoder 265 (Step 420).

The DTMF data may identify another program on the CD for playback. In such a case, the microcontroller 290 determines which program is indicated by the DTMF data (Step 470) and activates the playback of the indicated program in the CD player 280 (Step 475). Playback of the indicated program may then continue as if it was a selected program, and the user may move through the program using the playback selectors 160 and switch languages using the language selector 185.

Alternative Embodiments

The invention includes other aspects which provide further benefits. Another preferable aspect of the apparatus is a storage space for a second CD and overlay. The second compartment is also preferably easily accessibly by the ordinary user. The second CD could store programs for additional emergencies or languages.

In addition to information for medical and other emergencies, the apparatus and methods of the present invention are well suited for use in factories, schools, homes, etc. for training and for providing non-emergency information. Thus information on how to use machinery in a factory, or recipes for preparing food, can be carried and placed as desired.

Because of its portability, the device could be used to provide information to museum and park visitors, with the program selectors corresponding to particular attractions and sites.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

It is claimed:

1. A compact portable information apparatus, comprising:
a rigid casing which includes a handle;
a power supply including a battery;
a compartment accessible through a door in the casing by an ordinary user and adapted to receive a program medium, and permitting convenient removal of the program medium by the ordinary user;
a playback subsystem joined with the compartment within the casing, the playback subsystem adapted for playing back information stored in the program medium;
an input subsystem comprising a plurality of selectors each comprising a switch and a label, the selectors including a plurality of program selectors and a plurality of playback selectors disposed in the casing, wherein each program selector corresponds to one of a plurality of programs on the program medium, and the playback selectors include a selector for pausing playback of a program, a selector for stopping playback of a program, a selector for moving playback ahead in a program and a selector for moving playback back in a program;
an output subsystem disposed in the casing and coupled to the playback apparatus, the output subsystem outputting the stored programs to a user;
a control subsystem coupled to the playback subsystem and the input subsystem, the control subsystem responsive to user selection through the input subsystem to thereby control playback by the playback subsystem of programs on the program medium; and
a light sensor, the light sensor sensing when ambient lighting is below a predetermined level, and causing the switches and labels to be illuminated.

2. A compact portable information apparatus, comprising:
a playback subsystem adapted for playing back information stored in a program medium;
an input subsystem comprising a plurality of program selectors and a plurality of playback selectors, wherein each program selector corresponds to one of a plurality of programs on the program medium, and the playback selectors include a selector for pausing playback of a program, a selector for stopping playback of a program, a selector for moving playback ahead in a program and a selector for moving playback back in a program;
an output subsystem disposed in the casing and coupled to the playback apparatus, the output subsystem outputting the stored programs to a user;

a control subsystem coupled to the playback subsystem and the input subsystem, the control subsystem responsive to user selection through the input subsystem to thereby control playback by the playback subsystem of programs on the program medium; and a light sensor, the light sensor sensing when ambient lighting is below a predetermined level, and causing at least some of the playback selectors and the program selectors to be illuminated.

3. A compact portable information apparatus, comprising:

a removable program medium storing a DTMF encoded digital index and a plurality of programs, the programs comprising a plurality of steps including digitized verbal portions;

a playback subsystem adapted for controllably retrieving the index and the steps from the program medium;

an input subsystem comprising a plurality of program selectors corresponding to the programs on the program medium, and a plurality of playback selectors including a pause selector for pausing playback of a program, a stop selector for stopping playback of a program, an advance selector for moving playback ahead in a program and a repeat selector for moving playback back in a program;

an output subsystem coupled to the playback subsystem and including a speaker for outputting the verbal portions of the programs; and a control subsystem coupled to the playback subsystem and the input subsystem, the control system for decoding and storing the index, and responsive to user selection of the selectors to control playback by the playback subsystem of the programs by: identifying a selected selector, controlling the playback subsystem to advance to the identified step and controlling the playback apparatus to begin playback.

4. A compact portable information apparatus as set forth in claim 3 wherein the index includes conditions for the playback of predetermined steps and identification of such steps.

5. A compact portable information apparatus, comprising:

a playback subsystem for playing a program medium having digitized verbal programs comprising plural steps of irregular length, a digitized index and DTMF codes embedded in the verbal programs, the playback subsystem responsive to control signals at plural control inputs for determining the location of playback on the program medium and providing program output signals on plural program outputs;

an input subsystem comprising a plurality of program selectors and a plurality of playback selectors, each program selector corresponding to one of a plurality of programs on the program medium, and the playback selectors including a selector for pausing playback of a program, a selector for stopping playback of a program, a selector for moving playback ahead in a program and a selector for moving playback back in a program;

an output subsystem coupled to the program outputs of the playback subsystem, the output subsystem including means for converting the output signals into a form recognizable to a user; and a control subsystem comprising a DTMF decoder and a microcontroller, the DTMF decoder having inputs coupled to at least one of the program outputs of the playback subsystem and outputs coupled to the microcontroller for providing decoded DTMF control information from the program medium to the microcontroller, the microcontroller being coupled to the input subsystem to receive user selections and the control inputs of the playback subsystem for controlling the playback subsystem, the microcontroller being responsive to decoded DTMF control information for determining playback sequence, and responsive to user selection of the selectors to control playback by the playback subsystem of the programs by: identifying a selected selector, controlling the playback subsystem to advance to the identified step and controlling the playback apparatus to begin playback.

6. A compact portable information apparatus as set forth in claim 5 wherein the program selectors generate DTMF codes.

7. A compact portable information apparatus as set forth in claim 5 wherein the playback selectors generate DTMF codes.

8. A compact portable information apparatus as set forth in claim 5, wherein each program comprises a plurality of sequential instructions, and when the user selects the selector for moving playback ahead, the control subsystem causes the playback subsystem to move playback ahead by one instruction, and when the user selects the selector for moving playback back the control subsystem causes the playback subsystem to move playback back by one instruction.

9. A compact portable information apparatus as set forth in claim 5, wherein the casing is water resistant and includes water resistant seals.

10. A compact portable information apparatus as set forth in claim 5, further including a flashlight, wherein the handle has a longitudinal axis and the flashlight is aimed about 90° from the longitudinal axis of the handle.

11. A compact portable information apparatus as set forth in claim 5, further including a storage compartment accessible by the user, the storage compartment adapted to receive and secure an extra playback medium.

12. A compact portable information apparatus as set forth in claim 5, wherein the power supply includes a battery recharger.

13. A compact portable information apparatus as set forth in claim 12, wherein the battery recharger includes a standard electrical plug which plugs into an electrical outlet and removably secures the apparatus to the electrical outlet and supports the apparatus.

14. A compact portable information apparatus as set forth in claim 12, wherein the playback subsystem and the control subsystem are normally in a power-off state, and upon a user selection of a program using one of the program selectors, the control subsystem and the playback subsystem are provided power.

* * * * *